United States Patent [19]

White et al.

[11] 4,046,877

[45] Sept. 6, 1977

[54] METHOD OF INCREASING IMMUNOLOGIC COMPETENCE

[75] Inventors: Abraham White, Palo Alto; Pamela M. Burton, Cupertino, both of Calif.

[73] Assignee: Syntex (U.S.A.) Inc., Palo Alto, Calif.

[21] Appl. No.: 658,200

[22] Filed: Feb. 17, 1976

Related U.S. Application Data

[63] Continuation-in-part of Ser. No. 597,116, July 18, 1975, abandoned, which is a continuation-in-part of Ser. No. 561,409, March 24, 1975, abandoned.

[51] Int. Cl.$^2$ .............................................. A61K 37/00
[52] U.S. Cl. ....................................... 424/177; 424/85; 424/88; 424/101; 260/112.5 R
[58] Field of Search .............. 260/112.5 R, 16 B, 121; 424/177, 101

[56] References Cited

U.S. PATENT DOCUMENTS

| 3,560,475 | 2/1971 | Fekete et al. | 260/112 B |
|---|---|---|---|
| 3,850,903 | 11/1974 | Garcia et al. | 260/112 B |

FOREIGN PATENT DOCUMENTS

| 647,931 | 9/1962 | Canada | 260/112 B |

OTHER PUBLICATIONS

Kanda et al.: J. Biol. Chem., 249, 6796–6805 (1974).
Wara et al.: New England J. Med., 292, 70–74 (1975).

*Primary Examiner*—Delbert R. Phillips
*Attorney, Agent, or Firm*—Alan M. Krubiner

[57] ABSTRACT

Human serum prealbumin is shown to possess thymus hormone-like properties of increasing immunologic competence. Pharmaceutical compositions containing this material, useful for increasing immunologic competence, are described.

3 Claims, No Drawings

METHOD OF INCREASING IMMUNOLOGIC COMPETENCE

RELATED APPLICATIONS

This application is a continuation-in-part of our pending application Ser. No. 597,116, abandoned filed July 18, 1975, which in turn is a continuation-in-part of Ser. No. 561,409, filed Mar. 24, 1975, abandoned.

BACKGROUND OF THE INVENTION

The thymus has been recognized as an endocrine gland having a major function in the immunological defense system of the body. Recently, crude extracts of calf thymus have been shown to contain a family of hormones, referred to as thymosins, having molecular weights ranging from approximately 3,200 to 70,000 daltons. See for example, Trainin, N., *Physiological Reviews*, Vol. 54, p. 272 (1974) and White, A., *Ann. N.Y. Acad. Sci.*, Vol. 29, p. 253 (1975).

These hormones are believed to act by regulating the rate of maturation of incompentent, as yet unidentified, precursor cells to competent lymphocytes (T-cells) and thus to become effective fighters against foreign invaders. In addition, precursor cells of other types, e.g., erythroid, are stimulated in their production and maturation by thymosin preparations. Recently, a relatively crude calf thymus extract containing thymosin was used to increase the immunologic competence of a young girl born with impaired immunity. Wara, D.W., et al., *New Eng. J. Med.*, Vol. 292, p. 70 (1975). Also a recent report has described improvement in the total hematological status (increase in number of both white and red cells) in patients treated with a thymosin preparation. See Alexsandrowicz, J., et al., *Proc. Intl. Congress Immunol.*, Brighton, England, July 22–24, 1974.

There have also been reports, see for example Bach, J. F., et al., *Immunology*, Vol. 25, p. 353 (1973), that thymosin-like activity has been detected in fresh pig blood. The factor responsible therefor is believed to have a molecular weight of approximately 1,000 daltons.

DESCRIPTION OF THE INVENTION

The present invention is concerned with methods and pharmaceutical compositions useful for increasing immunologic competence.

In our earlier applications Ser. Nos. 561,409 and 597,116 we described the isolation and characterization of a protein having thymus hormone-like properties of increasing immunologic competence. This protein was described as having a molecular weight of approximately 56,700 daltons, as having the following approximate amino acid ratio:

| Amino Acid | Mole % |
| --- | --- |
| Aspartic Acid | 6.6 |
| Threonine | 9.5 |
| Serine | 9.3 |
| Glutamic Acid | 10.3 |
| Proline | 6.6 |
| Glycine | 8.3 |
| Alanine | 9.7 |
| ⅓ Cystine | 0.9 |
| Valine | 9.5 |
| Methionine | 0.7 |
| Isoleucine | 4.0 |
| Leucine | 5.9 |
| Tryosine | 2.3 |
| Phenylalanine | 3.9 |
| Tryptophan | 1.0 |

-continued

| Amino Acid | Mole % |
| --- | --- |
| Lysine | 6.3 |
| Histidine | 3.1 |
| Arginine | 3.2 | as having glycine and histidine as N-terminal amino acids; as having an isoelectric point of about 5.0 (now determined as being about 4.5); and being composed of four sub-units.

It has now been found that our previously described protein is identical with human serum prealbumin, a protein occuring naturally in human serum, which has previously been isolated, purified and identified by amino acid sequencing. (Cf. Kauda, Y., J. Biol. Chem., 249, 6796–6805, 1974).

Identification of the present protein as human prealbumin was made by a comparison of its physical and chemical properties with a commercially available sample and by cross reactivity with human prealbumin antibody.

While human prealbumin has previously been described, it has been thought to act merely as a specific carrier for several selected smaller molecules and has not been recognized as exhibiting any intrinsic biological activity. We have discovered, surprisingly, that human prealbumin has powerful thymic hormone-like properties of increasing immunologic competence. Examination of commercial samples of human prealbumin in selected bioassays, as described below, indeed shows that these materials possess the aforementioned biological activity, heretofore unrecognized.

Accordingly, one aspect of the present invention is concerned with a method of increasing immunologic competence by administering an effective amount of human serum prealbumin to a subject in need of said treatment.

A second aspect of the present invention is concerned with pharmaceutical compositions useful for increasing immunologic competence comprising a therapeutically effective amount of human serum prealbumin in admixture with a pharmaceutically acceptable non-toxic carrier.

A third aspect of the present invention is concerned with methods of isolation and purification of human serum prealbumin from human blood fraction Cohn IV-1.

As used in the specification and the appended claims the expression "immunologic competence" connotes the degree of responsivity of those physiologic mechanisms comprising immunity. Immunity endows the host with the capacity to neutralize, eliminate or metabolize foreign materials, e.g., bacteria, viruses and fungi, as well as cells of other animal species without injury to the host.

This expression is well known and accepted in the immunology art as illustrated, for example, in Bellanti, G.A., "Immunology", W. B. Saunders Co., Philadelphia, Pa., 1971. Two broad types of immunity are recognized, namely, humoral immunity based upon the production of soluble, circulating antibodies, and cell-mediated immunity based upon the production and functioning of specific types of lymphoid cells (lymphocytes). Mature lymphocytes participate in both humoral and cell-mediated immunity (cf., Gell, P. G. H. and Coombs, P. R. A., Clinical Aspects of Immunology, 2nd ed., F. A. Davis Co., Philadelphia, 1968; Miller, J.

F. A. P. and Osaba, D., Physiological Reviews, 47: 137, 1967; Trainin, N., Physiological Reviews, 54: 272, 1974; White, A., Ann. N.Y. Acad. Sci., 29, 253, 1975).

While not intending to be bound by any mechanism of action, it is believed that the present material acts by increasing both the number and rate of maturation of immunologically competent lymphocytes from precursor incompetent cells.

The enhancement of immunologic competence may be demonstrated by various indicia utilizing both in vitro and in vivo small animal bioassays well known in the immunology art. For example, the following assays may be especially mentioned:

1. In vitro azathioprine sensitive rosette assay (in vitro rosette assay)
2. In vivo azathioprine sensitive rosette assay
3. Antibody synthesis in vivo
4. Antibody synthesis in vitro
5. Proliferation of lymphoid tissue
6. Mixed lymphocyte reaction
7. Blastogenesis with concanavalin A
8. In vitro spontaneous rosette assay
9. Production of cytotoxic lymphocytes
10. Lymphocyte auto-sensitization in vitro
11. Lymphocyte auto-sensitization in vivo.

We have utilized each of the above bioassays to demonstrate the enhancement of immunologic competence by human prealbumin, as detailed in the Examples.

The above mentioned assays relate to one or more of the following general classes of clinical significance for which immunologic competence is believed to be a factor:

stimulation of antibody synthesis (especially assays 3 and 4)

replacement and restoration therapy (especially assays 5 – 9)

autoimmune diseases (especially assays 10 and 11).

The assay of choice for a rapid and accurate indication of activity for increasing immunologic competence is the well known above mentioned in vitro rosette assay as described by Bach, J.P., Proc. Natl. Acad. Sci. U.S.A., Vol. 68, p. 2334 (1971), wherein the sensitivity of spleen rosette forming cells to azathioprine [6-(1-methyl-4-nitro-5-imidazolyl)mercaptopurine]is measured.

This assay shows good correlation with the number of immunologically competent lymphocytes of the T-class. It is this class of lymphocytes that is involved in functioning cooperatively with B lymphocytes in antibody synthesis, and which are the prime cells that regulate cell-mediated immunity. A large volume of evidence supports the significance of this assay for assessing immunological status (cf. Bach. J.F., "The Mode of Action of Immunosuppressive Agents", North Holland-/American Elsevier Publishing Co., Amsterdam/New York, 1975).

Accordingly, human prealbumin may be useful clinically for human treatment in situations where immunologic competence is believed to be an important factor, for example, autoimmune diseases, (e.g., lupus erythematosus, ulcerative colitis, autoimmune hemolytic anemia, thyrotoxicosis, rheumatoid arthritis, hepatic cirrhosis) thymic aplasia and dysplasia, augmentation of immunity in infectious (e.g., bacterial, viral and fungal) disorders, Hodgkin's disease, hypogammaglobulinemic syndrome, aberrant cell proliferative conditions, decrease in immunologic competence due to temporal decline in thymic hormone production, in chemical or radiologically induced immuno-suppressed states, and so forth.

It has been found that, when essentially free from impurities, human prealbumin prepared as described below exhibits activity in the in vitro rosette assay at levels below one nanogram.

While it is desirable for many purposes to utilize essentially pure human prealbumin in a suitable composition for therapeutic administration, the tedious purification and preparation of the pure material in large quantities, necessitating considerable loss of material and the attendant expense and effort, make it desirable to utilize, for many therapeutic purposes, less pure fractions containing human prealbumin, providing that such fractions are free of cytotoxic impurities. Thus, it has been found that partially purified fractions exhibiting activity in the in vitro rosette activity at approximately 0.01 to 0.20 micrograms, are highly useful for therapeutic purposes.

Human prealbumin, either in essentially pure form or as a component of a partially purified fraction free of cytotoxic impurities, may be made up in the form of conventional pharmaceutical or medicinal preparations by admixture with pharmaceutically acceptable, non-toxic excipients. For example, the material can be mixed with organic or inorganic inert pharmaceutical carriers suitable for parenteral administration, for example, intramuscularly, subcutaneously, or intravenously in the form of, for example, liquid solutions, suspensions, and the like, in unit or divided dosages.

The pharmaceutical compositions containing the present material may be subjected to conventional pharmaceutical expedients such as sterilization (e.g. by millipore filtration) and can contain conventional pharmaceutical excipients such as preservatives, stabilizing agents, emulsifying agents, bulking/binding agents, salts for the adjustment of osmotic pressure, or buffers. The compositions may also contain other therapeutically useful materials, or materials which prolong the duration of action of the present compound. Actual methods of preparing such dosage forms are known or will be apparent to those skilled in the art. An extensive compilation of such formulation techniques may be found, for example, in "Remington's Pharmaceutical Sciences" by E. W. Martin. One preferred method for preparing formulations ccontaining the present material is by reconstitution of lyophilized human prealbumin. Thus, human prealbumin prepared as described hereinbelow may be sterilized and lyophilized either solely or with other solid excipients, and stored in a sterile vial until needed. Immediately prior to administration, the desired amount of solvent, e.g. water, water containing preservatives, or a solution of various excipients in water, is added to dissolve the human prealbumin.

In any event, the pharmaceutical composition to be administered will contain a quantity of human prealbumin in a therapeutically effective amount for treatment of the particular condition of concern.

The dosage regimen may consist of unit or divided dosages, but in any event will necessarily be dependent upon the needs of the subject being treated and the judgment of the attending medical practitioner. However, as a broad guideline for most purposes, the present essentially pure material will be administered in the range of from about 10 pg/kg/day to about 20 µg/kg/day, preferably from about 100 pg/kg/day to about 3 µg/kg/day. Expressed in alternate terms for an average (70 kg) adult human subject this would be from about 0.7 ng/day to about 1.4 mg/day, preferably from about 7 ng/day to about 0.2 mg/day or on a schedule determined by results of initial daily treatment at the above level. A less pure fraction will necessarily be administered in correspondingly higher dosage.

Human prealbumin may be isolated either as a component of a partially purified fraction, free of cytotoxic impurities, or in essentially pure form, starting with human blood or a readily available human blood fraction by means of a multi-step purification procedure.

A particularly valuable source of human prealbumin is the human blood fraction known as the Cohn IV-1 fraction, which is obtained, and generally discarded as a waste fraction, during the fractionation of human blood. This fraction is thus available in large quantities from blood sources and is relatively inexpensive. On the average, the Cohn IV-1 fraction exhibits activity in the in vitro rosette assay at approximately 24 micrograms. In terms of activity in the rosette assay, the Cohn IV-1 fraction represents approximately a ten-fold purification from crude human serum. Thus, pure human prealbumin exhibiting activity in the rosette assay below 1 nanogram, typically from 0.2 to 1.0 nanogram, represents a 24,000 to 120,000-fold enhancement of activity as compared with the Cohn IV-1 fraction, and a 240,000 to 1,200,000-fold enhancement of activity as compared with crude human serum. This enhancement in activity is believed due, in part, to the removal of an inhibitory fraction normally present in serum. The complex purification procedure necessary to achieve such a remarkable degree of enhancement of activity, and to render the resultant material essentially pure, is described below.

The procedure for the purification of the human prealbumin, starting with the Cohn IV-1 fraction involves the following steps:
1.a. Molecular filtration to exclude high molecular weight material and low molecular weight material, or b. Ammonium sulfate fractionation,
2. Gel chromatography,
3. Repeat of step 2, or free-flow electrophoresis,
4. Preparative gel electrophoresis, and
5. Gel chromatography.

During each stage of the purification procedure the various fractions which are generated are routinely assayed, preferably using the in vitro rosette assay, to determine the thymus hormone-like activity. The fraction or fractions containing the major part of such activity are further processed in the later stages, thus concentrating the active fractions into smaller and smaller volumes, while separating the active component from inactive impurities, until the desired material is obtained in essentially pure form.

While preferred embodiments of the purification steps outlined above are described in Examples 1 and 9, a brief description of the purification procedure is presented below:

The crude Cohn IV-1 fraction may optionally be lyophilized, if desired. This is conveniently done by suspending the crude Cohn IV-1 fraction in distilled or deionized water, stirring to break up lumps, and then removing solvent and other volatiles under reduced pressure.

The lyophilized material has greater stability and may be stored in the cold for extended periods. Prior to purification, the crude or lyophilized Cohn IV-1 fraction is made up as an aqueous solution and preferably centrifuged to remove sediment.

For molecular filtration, distilled or deionized water is used as solvent, preferably adjusting the pH to about 7.0, and for ammonium sulfate fractionation, an aqueous buffer is utilized.

In one embodiment of the present process Cohn IV-1 fraction (crude or, preferably, lyophilized) in solution in distilled or deionized water, is subject to two molecular filtrations so as to remove components having molecular weights substantially above and below that of the desired component. A suitable molecular filtration technique involves, initially, the passage of the above mentioned solution through a hollow fiber fractionator with a suitable membrane filter to remove components of high molecular weight (greater than about 60-70,000 daltons, depending upon filtration pressure). Suitable hollow fiber fractionators are (depending upon volume of substrate) the Amicon DC-2 and DC-30 fractionators. In using the DC-2 fractionator, a suitable membrane filter is the Amicon HIDX-50. With the DC-30 fractionator, a suitable filter is the Amicon HIOX-50.

The filtrate from the above molecular filtration is subjected to another molecular filtration to remove low molecular weight materials. Thus, passage through a similar hollow fiber fractionator fitted with a membrane to retain material of molecular weight of approximately 10,000 daltons or higher, results in the desired material, having a molecular weight of approximately 56,700 daltons, being isolated from the retentate. A suitable filter for this purpose with the DC-2 apparatus is the Amicon HIDP-10, and with the DC-30 apparatus, the Amicon HIOSM.

Alternatively, the filtration procedure may be reversed so that first low molecular weight, then high molecular weight, impurities are removed. The former procedure is preferred.

In a second, and preferred, embodiment, the crude or, preferably lyophilized, Cohn IV-1 fraction is subjected to ammonium sulfate fractionation. By this procedure a much higher (approximately 8-fold) yield of desired material is obtained compared to the molecular fractionation techniques described above.

The Cohn IV-1 fraction is first dissolved in a suitable buffer having a pH between about 7.8 and 8.2 such as Tris [commonly known as tris (hydroxymethyl) aminomethane]-sodium azide and preferably centrifuged to remove sediment. The solution is then treated at a temperature between about 0° and 5° C., sequentially with portions of ammonium sulfate, to "salt out" various fractions. After each addition of ammonium sulfate, the precipitate formed is separated from the supernatant, which is then further treated with ammonium sulfate.

The fraction containing the desired material is "salted out", or precipitated, when ammonium sulfate is added such as to bring the ammonium sulfate content of the solution up from about 40 to about 60 percent of saturation. The quantity of ammonium sulfate necessary to reach the appropriate degree of saturation may be readily determined from solubility tables.

The precipitate containing the desired material is preferably desalted by techniques well known in the art, for example by diafiltration or preferably by dialysis of a solution of the precipitate in distilled water. The desalted material is then concentrated in preparation for the next step by, for example, lyophilization from the frozen state.

In the next step, the desired material from the previous molecular filtration or ammonium sulfate fractionation is subjected to chromatography on a polysaccharide gel column which fractionates components applied thereto by molecular weight. Suitable columns are those prepared from cross-linked dextrans such as Sephadex G-75, G-100, G-150 or G-200 (Pharmacia Fine Chemicals). A preferred material is Sephadex G-150, as it affords an optimum separation of components as determined by examination of the $K_{av}$ versus log molecular weight curve (see Andrews, *Biochem. J.*, Vol. 91, p. 222, 1964). Such a gel chromatography is suitable carried out by passing through the loaded column an aqueous elution buffer having a pH of approximately 7.8 to 8.2, preferably about pH 8.0. A suitable buffer is Tris-NaCl-NaN$_3$. The temperature should be between about 0° and 10° C., preferably about 5° C. Eluent fractions are collected from the gel chromatography and the fraction(s) containing the desired component may be determined by ultraviolet absorption, total protein eluted and/or bioassay. The column may be calibrated so that the eluent fraction containing the desired molecular weight range may be readily determined (see Andrews, cited above).

The desired fraction(s) is preferably desalted by dialysis or preferably by diafiltration and concentrated in preparation for the next step by, for example, lyophilization. The diafiltration is carried out under pressure (e.g. 70–80 psi nitrogen) through a membrane with the appropriate pore sizes, so that the desired material is retained. Suitable membranes that may be mentioned are the Amicon UM-05 and UM-10, having molecular weight cut-off ranges of 500 and 10,000, respectively. Other membranes that could be used are the Amicon UM-2, PM-10 or UM-20E.

In the next step, the above material from the gel chromatography is either recycled through the same or similar gel column or, alternatively, is subjected to free-flow electrophoresis. The free-flow electrophoresis is carried out according to procedures known per se in the art. The pH should be between about 5.0 and 5.5, preferably about 5.25. A preferred buffer for establishing such pH is sodium acetate-acetic acid. The locations of the desired component may again be established by the use of ultraviolet absorption, total protein and/or biosassay methods, and/or by use of a calibrated column.

The desired material obtained from the previous step is then subjected to preparative polyacrylamide disc gel electrophoresis, in the usual manner for such procedure. It is preferred that such electrophoresis be carried out in a manner such that the separator gel and the elution buffer are at a pH between about 8.5 and 9.5, preferably about 8.9. A preferred buffer for establishing such pH is Tris-HCl. Normally, after this procedure, there is obtained electrophoretically homogeneous human prealbumin. The homogeneity of the component obtained may be determined by standard analytical techniques such as the use of analytical disc-gel electrophoresis or isoelectric focusing, and the hormonal activity may be determined by bioassay. As a final step, the material is freed from polyacrylic acid and residual salts by chromatography as described above, on a micro-polysaccharide column, preferably of Sephadex G-75. The first peak that elutes from the column contains the active material as judged by the above mentioned criteria, and the product itself may be obtained by lyophilization.

In the following specific examples there are described the preparation of both essentially pure and partially purified human prealbumin, as well as descriptions of the bioassays utilized and the results obtained therefrom. It should be recognized by those skilled in the art that the descriptions contained herein are illustrative only of the invention and should not be construed as limiting the scope or spirit of the invention in any manner.

The literature cited above and in the examples is hereby incorporated by reference and made a part hereof.

EXAMPLE 1

Purification of human prealbumin from Cohn fraction IV-1

Four kilos of Cohn human blood fraction IV-1 (Cutter Laboratories) were stirred in 20 l. of double distilled water at 5° C. for four hours and lyophilized to afford 1105 g. of dry material which was suspended in ten volumes of deionized water. The pH was adjusted to 7.0 with ammonium hydroxide and the mixture stirred for one hour at room temperature. The sediment was removed and the supernate passed through an HIOX-50 cartridge in an Amicon DC-30 apparatus. The lower molecular weight fraction from this step was then passed through an HIOSM cartridge in the same apparatus. After lyophilization of the retentate there was obtained 50 g. of material which was chromatographed, in one gram portions, (after dissolution in the below-mentioned buffer) on a 5 × 90 cm. G-75 Sephadex (Phamacia Fine Chemicals) column equilibrated with 50 mM Tris-100 mM NaCl-0.02% sodium azide buffer, pH 8.0, at 5° C. The chromatography was monitored by optical density measurements at 280 nm, the contents of each tube were lyophilized and diafiltered to determine total protein, and then subjected to an in vitro rosette assay. Over 90% of the activity eluted was recovered in a fraction slightly retarded on this column with a $K_{av}$ value of 0.055, corresponding to an approximate molecular weight range of about 50,000 to 70,000 daltons. This material (total from all one gram runs = 20 g.) was then subjected to free-flow electrophoresis at pH 5.25 in an acetate buffer system (25 mM NaOAc - 7 mM HOAc). As above, the progress was monitored by optical density, total protein and bioassay. The material resulting from combination of active fractions was further purified by preparative polyacrylamide gel electrophoresis using a 10% cross-linked gel. The spacer and sample gels were 0.060 M in Tris, adjusted to pH 6.6–6.8 with HCl. The separator gel was 0.375 M in Tris, adjusted to pH 8.9 with HCl. The electrode vessel buffer was 0.024 M in Tris and 0.192 M in glycine, pH 8.2–8.4. The elution buffer was 0.375 in Tris, adjusted to pH 8.8–9.0 with HCl. The activity was eluted in a fraction migrating between the tracking dye (Bromophenol Blue) and the albumin fraction. This material (approximately 100 mg. total) was electrophoretically homogeneous when run in an analytical system at pH 8.9.

Repeat of the Sephadex chromatography, as described above, on a micro (0.8 × 76 cm.) column afforded essentially pure prealbumin as a white solid.

The $S_{20w}$ value determined by sedimentation velocity in the Spinco model E ultracentrifuge was found to be 4.07 and the molecular weight of the molecule determined by sedimentation equilibrium was found to be 56,700 daltons. After treatment with 5M guanidinium-hydrochloride - 0.8% dithiothreitol -0.01M phosphate buffer pH 5.2 followed by 5N urea - 0.1% sodium dodecyl sulfate - 1% dithiothreitol -0.01M phosphate buffer pH 7.4 followed by electrophoresis at pH 7.0 in a sodium dodecylsulfate - containing acrylamide gel, the molecular weight of the undissociated material was found to be 52,000 daltons and there was partial dissociation into four sub-units with a molecular weight of approximately 13,500 daltons each.

The protein was homogeneous upon isoelectric focusing in polyacrylamide gel containing ampholines with a pH range of 3-10, and possessed an approximate isoelectric point of 4.5. N-terminal analysis obtained by dansylation indicated the presence of derivatives corresponding to dansyl glycine and α-dansyl histidine. Amino acid composition was determined by hydrolysis of the protein and chromatography on a Durrum amino acid analyzer under standard conditions and afforded the following composition.

| Amino Acid | Mole % |
| --- | --- |
| Aspartic Acid | 6.6 |
| Threonine | 9.5 |
| Serine | 9.3 |
| Glutamic Acid | 10.3 |
| Proline | 6.6 |
| Glycine | 8.3 |
| Alanine | 9.7 |
| ½ Cystine | 0.9 |
| Valine | 9.5 |
| Methionine | 0.7 |
| Isoleucine | 4.0 |
| Leucine | 5.9 |
| Tryosine | 2.3 |
| Phenylalanine | 3.9 |
| Tryptophan | 1.0 |
| Lysine | 6.3 |
| Histidine | 3.1 |
| Arginine | 3.2 |

Identity was further established by comparison with authentic samples of human prealbumin.

EXAMPLE 2

In vitro rosette assay during purification of human prealbumin

The in vitro rosette assay, was performed essentially as described by Bach, J.F., et al, *Proc. Natl. Acad. Sci. U.S.A.*, Vol. 68, p. 2734 (1974). The exact protocol was as follows:

A. Preparation of azathioprine sodium salt stock solution

277 Mg. of azathioprine free acid, (Imuran, Burroughs Wellcome), was dissolved in 25 ml. of water in a volumetric flask. Approximately 1 ml. of 1N NaOH was added dropwise with stirring to dissolve all of the powder. The final solution was diluted 1:100 in Hank's balanced salt solution, pH 7.2, prepared from powdered medium (Difco Labs., Detroit, Mich.) to afford a solution containing 0.106 mg./ml. of azathioprine sodium salt, pH 8.2. This solution was filtered through a millipore filter to effect sterilization. The final solution was stored away from light in a refrigerator. Stability was checked by measuring optical density at 280 and 330 nm.

B. For the assay itself, spleen cells from 6-8 week old male C57B1/6 Simonsen mice thymectomized 7-30 days prior to sacrifice were used. Individual spleens were homogenized and washed in cold Hank's balanced salt solution. The cells were pelleted at 200 × g for ten minutes in a refrigerated centrifuge. A final pooled suspension of 40-60 × $10^6$ nucleated cells per ml. was prepared.

Control series to determine the sensitivity of thymectomized spleen cells to azathioprine sodium salt, the azathioprine sodium salt was titrated, ranging from 25 μg./tube to 1.56 μg./tube, using 2-fold serial dilutions of 0.25 ml. of stock solution (part A) in Hank's. Spleen cell suspension prepared above (0.1 ml.) was added to each dilution (4.6 × $10^6$ cell/tube).

Test series test fractions of human prealbumin (0.125 ml. aliquots) were serially diluted 2-fold in Hank's. 2.5 Micrograms azathioprine sodium salt in 0.125 ml. of Hank's (see above) and 0.1 ml. of spleen cell suspension, were added to each dilution of the test fraction.

Both the control and the test series were incubated at 37° C. in water bath for 60 minutes. 0.2 Ml. of 50% sheep erythrocytes (SRBC) in Alsever solution (Grand Island Biological Co., "Gibco", Grand Island, N.Y.), prepared 2 days previously, was diluted in 15 ml. Hank's. 0.125 Ml. of this SRBC suspension was added to each tube in both series, and the cells were pelleted in a refrigerated centrifuge at 200 × g for 5 minutes. Pelleted cells were refrigerated at 4° C. for 90 minutes, gently resuspended on a rotator for five minutes and the rosettes counted in a Malessez hemocytometer.

The specific activity was determined by the minimum quantity of protein in the test fractions that inhibited rosette information by 50% or more in the presence of 2.5 μg./tube of azathioprine sodium salt. The specific activity of the fractions obtained during purification (Example 1) is shown in the following chant, as is a relative purification factor, using the Cohn IV-1 fraction as a reference.

| Step | Fraction | Activity in rosette assay (μg of protein) | Purification factor |
| --- | --- | --- | --- |
| 1. | Cohn fraction IV-1 | 24 | 1 |
| 2. | DC-30 HIOSM cartridge retentate | 3 | 8 |
| 3. | Chromatography on Sephadex G-75, pH 8, fraction 2 | 0.1 | 240 |
| 4. | Free-flow electrophoresis, pH 5.25, fraction 2 | 0.01 | 2,400 |
| 5. | Preparative polyacrylamide gel electrophoresis pH 8.9, fraction 1 | 0.002 | 12,000 |
| 6. | Chromatography on micro-Sephadex G-75, fraction 1 | 0.0004 | 60,000 |

The above chart demonstrates the use of the in vitro rosette assay to monitor the purification of human prealbumin, and demonstrates that a 60,000-fold purification (based on activity) from Cohn fraction IV-1 has been achieved.

EXAMPLE 3

Stimulation of antibody synthesis

When normal animals, or animals that are experimentally depressed in their immunological responsivity, are injected with a foreign antigen, e.g., a protein obtained from another species, stimulation occurs of an immunological defence mechanism, e.g., synthesis of antibodies that have the capacity to "neutralize" the foreign material.

Protocol: Normal mice (C57B1/6 strain) were treated, by a single intravenous injection, with sheep erythrocytes (SRBC) as an antigenic stimulant. At the same time the test mice were injected intravenously with a quantity of human prealbumin (an appropriate fraction as depicted on the chart in Example 2). Control mice received the antigen and bovine serum albumin (BSA). Seven days later the animals were killed, the spleens dissected out and each spleen utilized for antibody assay in vitro according to the method of Jerne, H.K., et al, Science, Vol. 140, p. 405 (1963). The antibody response is expressed as the number of plague forming cells (PFC) per $10^6$ spleen cells.

A. The following chart illustrates antibody formation utilizing a human prealbumin fraction ("hormone") corresponding to step 2 from the chart in Example 2. Both 19S(IgM) and 7S(IgG) antibodies were assayed.

| Material Injected | PFC/$10^6$ Spleen Cells | |
|---|---|---|
| | 19S(IgM) | 7S(IgG) |
| Saline | 33 | 2 |
| SRBC | 105 | 114 |
| SRBC + 10 μg. hormone | 193 | 112 |
| SRBC + 100 μg. hormone | 249 | 173 |
| SRBC + 400 μg. hormone | 276 | 310 |
| Saline + 400 μg. hormone | 1 | 1 |
| Saline + 400 μg. BSA | 3 | 1 |
| SRBC + 10 μg. BSA | 120 | 119 |
| SRBC + 100 μg. BSA | 154 | 76 |
| SRBC + 400 μg. BSA | 156 | 152 |

The data show that the human prealbumin administration increased significantly the capacity of spleen cells to synthesize 7S and 19S antibody.

B. The effect of human prealbumin ("hormone") on antibody synthesis can also be demonstrated in an in vitro assay. In this case spleen cells from C57B1/6J mice were cultured and were then treated either with sheep erythrocytes, sheep erythrocytes plus hormone, or hormone alone. The hormone utilized in this experiment was from step 3 from the chart in Example 2. The antibody response was measured after five days of culture. Only the 19S antibody was measured. The results are expressed in the following chart.

| Material added to spleen cell culture | 19S Antibody response (PFC/$10^6$ spleen cells) |
|---|---|
| — | 46 |
| SRBC | 1332 |
| SRBC + hormone (10 μg.) | 2097 |
| SRBC + hormone (50 μg.) | 1964 |
| Hormone (50 μg.) | 58 |

The above results demonstrate that the human prealbumin preparation was active in stimulating IgM(19S) antibody synthesis when added in vitro.

EXAMPLE 4

Effect of human prealbumin in neonatally thymectomized mice

It is well established that neonatal thymectomy produces an "immunologic cripple". The operated animals fail to grow normally, show wasting and have little resistance to infections, can not synthesize antibody in response to challenge by specific antigens, and have no cell-mediated immunity, i.e., cannot reject a skin graft from an allogenic strain of the same species. Generally such operated animals die within five to ten weeks post-operatively from generalized infections, depending upon the degree to which the environment in which they are housed is free of infectious agents. This neonatal thymectomy syndrome has been demonstrated in a variety of species and is also seen in children born either without a thymus or with thymic aplasia or dysplasia, Miller, J.F.A.P., et al., Physiol. Revs., Vol. 47, p. 137 (1967) and Trainin, N., Physiol. Revs. Vol. 54, p. 272 (1974).

Protocol

C57B1Ka mice were thymectomized within 24 hours of birth utilizing surgically sterile techniques and housed under conditions free of specific infectious pathogens. Groups of ten each of these neonatally thymectomized mice were treated as indicated below. Bovine serum albumin (BSA) was used as a control protein.

A. Antibody synthesis

Beginning nine weeks post-thymectomy, each mouse was injected intraperitoneally on alternate days (total of eight injections) with 1 mg. per injection per mouse of either a humal prealbumin preparation ("hormone") or BSA. The hormone utilized for this experiment was that from step 2 from the chart in Example 2. The animals were sacrificed one week after the last injection or hormone and five days after a single intraperitoneal injection of the antigen, sheep erythrocytes. Antibody titers (19S) were determined according to the method of Mishell, R. I., J. Exp. Med., Vol. 126, p. 423 (1967). The results are expressed in the table below.

| 19S Antibody Response (PFC/$10^6$ Spleen Cells | |
|---|---|
| Hormone Treated Mice | BSA Treated Mice |
| 58,650 | 9,500 |

The above chart demonstrates that the administration of the human prealbumin preparation restored to neonatally thymectomized mice the ability to synthesize 19S antibody in a response to a challenge of sheep erythrocytes, a thymic dependent antigen.

B. The mixed lymphocyte interaction

When lymphoid cells of mice of a specific strain are mixed in vitro with lymphiod cells of mice from an unrelated strain, the "foreign" nature, from an immunological point of view, of the cells to one another results in a proliferative response of each cell. As indicated below, one of the two cell populations can be prevented from proliferating, or undergoing blastogenesis by adding to one cell population prior to mixing, an agent that inhibits cell division. The ability of cells to recognize foreign cells is a reflection of a cell-mediated, immunological response. This is the so-called "one way" mixed lymphocyte reaction.

Lymphoid cells from neonatally thymectomized mice or from genetically thymusless (nude) mice are incapable of this type of recognition, i.e., do not react in the mixed lymphocyte reaction when incubated with lymphoid cells from adult mice of another strain.

The protocol used was that described by Goldstein, A. L., et al., J. Immunol., Vol. 106, p. 773 (1971).

The data shown below were obtained with lymph node cells from neonatally thymectomized C57B1/Ka mice treated at four weeks of age with single subcutaneous injections, over a two week period, of 1 mg. each of "hormone" corresponding to Step 2 from the chart in Example 2. A control group of neonatally thymectomized C57B16/Ka mice received similar doses of 1 mg. of bovine serum albumin. The animals were then sacrificed and the lymph nodes (mesenteric, axillary and inguinal) and spleens dissected out. Cell suspensions of lymph nodes of each mouse were tested in the mixed lymphocyte reaction, using equal numbers of C57B16/Ka lymph node cells (A) and allogenic (BLA) cells (B). "Background" incorporation for each cell type was obtained separately and subtracted from the mixed cell reaction value to afford the difference in counts per minute ($\Delta$CPM), resulting from the interaction of the two cell types.

The data obtained were as follows:

| Treatment | $^3$H-Thymidine Incorporation | |
|---|---|---|
| | $\Delta$CPM$^1$ | Stimulation Index$^2$ |
| Bovine Serum Albumin | 11,596 | 28.4 |
| Hormone | 18,358 | 48.8 |

$^1\Delta$CPM = A $\times$ B $-$ (A + B)
$^2$Stimulation index = $\frac{A \times B}{A + B}$ It is clear that the lymph node cells from the animals treated with the human prealbumin preparation showed an approximately two-fold increase in the stimulation index. These data indicate that the cells from the neonatally thymectomized mice treated with this preparation were significantly enhanced in their immunological competence as reflected in their capacity to "recognize" lymph node cells of an histoincompatible strain of mice.

EXAMPLE 5

Proliferation of Lymphoid Tissue

Mice deprived of their thymus gland within 24–48 hours of birth (neonatal thymectomy) or genetically athymic (nude) mice fail to develop normal lymphoid tissue. That is, their lymph nodes and spleen (the lymphoid organs) are small and show a paucity of lymphocytes. This is a reflection of the fact that early in life, the thymus produces large numbers of lymphoid cells that are exported to, and seed, the peripheral lymphoid organs when these cells proliferate. This normally results in growth and maturation of normal lymphoid structures.

Protocol

Genetically athymic (nude) mice 4 weeks of age were given 8 daily subcutaneous injections of 1 mg. of human prealbumin preparation ("hormone") corresponding to Step 2 from the chart from Example 2 over a two week period prior to sacrifice. Control mice received injections of 1 mg. bovine serum albumin. The lymph nodes (mesenteric, inguinal and axillary) were dissected out, blotted, pooled and the number of total lymphoid cells counted. The data are as follows:

| Tissue | Bovine Serum Albumin No. of Cells | Hormone No. of Cells |
|---|---|---|
| Spleen | 1.02 $\times$ 10$^8$ | 1.8 $\times$ 10$^8$ |
| Lymph Nodes | 21.3 $\times$ 10$^6$ | 41.5 $\times$ 10$^8$ |

It may be noted that proliferation of lymphoid cells in normal mice is known to be under thymic regulation. The genetically thymusless (nude) mouse has small, undeveloped lymphoid tissue. The above data indicate an increase in human prealbumin treated mice of numbers of lymph node cells by a factor of $\sim$2 $\times$ 10$^2$, i.e., a 200-fold increase.

EXAMPLE 6

Stimulation by Mitogens: Blastogenesis on Exposure to Concanavalin A

Lymphoid cells from nude mice, because they are immunologically unresponsive, do not respond to concanavalin A, a mitogen known to act on immunologically competent T-cells, to accelerate their maturation and differentiation.

Protocol

Treatment of nude mice was as described for proliferation of lymphoid tissue (Example 5) using the same preparation and quantity of human prealbumin. The assay used is described by Claman, H. N., J. Immunol., Vol. 112, p. 960 (1974) based upon the incorporation of $^3$H-thymidine into lymphoid cells incubated in vitro with and without addition of concanavalin A (Miles-Yeda, Kankakee, Ill.)

| Data obtained: | CPM* |
|---|---|
| Cells from BSA treated mice + phosphate-ringer buffer + concanavalin A | 110 |
| Cells from hormone treated mice + phosphate-ringer buffer + concanavalin A | 419 |

*Average of $^3$H-thymidine incorporated per single incubation tube.

Injection of the human prealbumin preparation increased by approximately 4-fold the mitogenic response of the cells to concanavalin A. Thus, administration of this material to nude mice increased the number of host cells exhibiting T-cell properties in their responsivity to the mitogen.

EXAMPLE 7

In vitro Maturation of Human Lymphocytes to Immunologically Competent T-cells

The numbers of spontaneous erythrocyte (E) rosette forming cells in peripheral blood lymphocytes is one index of host immunological competence since this index reflects the number of circulating, immunologically competent T-cells.

In normal individuals, the number of E rosette cells in the peripheral blood generally represents 65–80% of the total lymphocyte population. Values below this range are often observed in immunologically deficient states, including malignant diseases, thymic aplasia or dysplasia, rheumatoid arthritis, etc.

Protocol

Lymphocytes were separated from human peripheral blood on a Ficoll-Hypaque gradient, Boyun, A., Scan. J. Clin. Lab. Invest., Vol. 21: Supl. 97, (1968). T-lymphocytes were identified by spontaneous rosette formation with sheep erythrocytes, Bentwich, Z., et al, Clin. Immunol. Immunopath., Vol. 1, p. 511 (1973). A change of $\pm$10% (on a scale of 100%) is considered significant. The data obtained are as follows:

| Lymphocytes from | Initial % | +50 $\mu$g. | +Inhibitory Spleen Extract | +RIS$^{(1)}$ +50 $\mu$g. |
|---|---|---|---|---|
| Seven Normal | | | | |

-continued

INFLUENCE OF HUMAN PREALBUMIN (HORMONE CORRESPONDING TO STEP 3, CHART, EXAMPLE 2) IN VITRO ON PERCENT OF SPONTANEOUS ERYTHROCYTE (E) ROSETTE FORMING CELLS IN PERIPHERAL BLOOD LYMPHOCYTES OF NORMAL INDIVIDUALS AND PATIENTS WITH HODGKIN'S DISEASE

| Individuals | E Rosettes | Hormone | (RIS)[1] | Hormone |
|---|---|---|---|---|
| 1 | 70 | 70 | N.D.* | N.D.* |
| 2 | 65 | 65 | N.D. | N.D. |
| 3 | 61 | 68 | N.D. | N.D. |
| 4 | 66 | 55 | N.D. | N.D. |
| 5 | 66 | 60 | 47 | 68 |
| 6 | 68 | 69 | 48 | 64 |
| 7 | 72 | 69 | 50 | 71 |
| Lymphocytes from Six Patients with Hodgkin's Disease | | | | |
| 1 | 67 | 66 | N.D. | N.D. |
| 2 | 62 | 72 | N.D. | N.D. |
| 3 | 48 | 70 | N.D. | N.D. |
| 4 | 55 | 70 | N.D. | N.D. |
| 5 | 62 | 78 | 43 | 66 |
| 6 | 43 | 70 | 50 | 54 |

*N.D. = Not done
[1]10 μg. protein/assay tube

The above results suggest that in vitro incubation with the human prealbumin preparation of separated, peripheral blood lymphocytes from individuals that have lower than normal percentages of spontaneous E rosette forming cells results in an increase in the percentage of these cells. Such data have been interpreted to indicate that inadequate thymic hormone concentration is the basis for the lower numbers of E rosette forming cells in these clinical conditions. In contrast, precursor cells are apparently present in these individuals since incubation of these cells with added human prealbumin preparation increases the number of spontaneous E rosette forming cells.

Hodgkin's disease patients frequently show lower than normal numbers of spontaneous E rosette forming cells. The above data reveal that peripheral lymphocytes of 5 l out of 6 of the Hodgkin's patients studies showed, on incubation with human prealbumin preparation, a significant increase in the percent of spontaneous E rosette forming cells.

In addition, the human prealbumin preparation counteracted the inhibitory effect of an extract of spleen from Hodgkin's patients on the numbers of spontaneous E rosette forming cells in the peripheral blood lymphocytes of normal individuals and in one patient with Hodgkin's disease.

EXAMPLE 8

Activity of Human Prealbumin Preparation In Vivo

The above sheep rosette forming cell assay referred to in Example 2, was applied also in assays in which a highly purified human prealbumin preparation (corresponding to Step 6 from the Chart in Example 2) was administered in vivo. The protocol was as follows:

The preparation to be assayed was administered to normal adult C57B1/6 mice (6-8 weeks of age) that had been thymectomized two weeks prior to use. Daily injections on each of three successive days were given intraperitoneally in doses of 2-4 μg. per mouse.

Twenty-four hours following the last injection, the animals were sacrificed, the spleens quickly removed, cell suspensions prepared and used in the rosette assay. The data are represented below:

| | End Point |
|---|---|
| Normal mouse, not thymectomized | 0.78 μg. azathioprine |
| Thymectomized mouse, injected with saline | 25 μg. azathioprine |
| Thymectomized mouse, injected with 2 μg. preparation | 0.195 μg. azathioprine |
| Thymectomized mouse, injected with 4 μg. preparation | 0.098 μg. azathioprine |

The above data show that immunological competence was restored to the spleen cells of thymectomized mice by the administration of the preparation. It should be noted that injection of the purified human prealbumin preparation restored to spleen cells of thymectomized mice a sensitivity to the inhibitory effects of azathioprine, based upon numbers of spleen rosette forming cells, equal to that of normal mouse spleen cells. The absolute activity of the preparation used in this assay is, in the in vitro assay, 0.4 ng.

EXAMPLE 9

Alternate purification of human prealbumin from Cohn fraction IV-1.

100 G. of Cohn fraction IV-1 (wet weight) is stirred with 500 ml. of distilled water for 4 hours at 2°-5° C. The suspension is then lyophilized, yielding approximately 40 g. of a dry powder. This material is then dissolved in 1,000 ml. of 50 mM Tris-100 mM sodium chloride - 0.02% sodium azide buffer, pH 8.0, and stirred for 3 hours at room temperature. The solution is then centrifuged at 13,000 × g. for 30 minutes at 2°-5° C. The clear greenish supernatant in a suitable container surrounded by ice is then made 40% saturated with ammonium sulfate by the addition of 243 g. of ammonium sulfate to 1,000 ml. of the supernatant. The suspension is allowed to settle at 5° C. overnight and the precipitate removed by centrifugation. The supernatant is then made 60% saturated with ammonium sulfate by the addition of 132 g. of ammonium sulfate to 1,000 ml. of the supernatant and the precipitate collected as before. The precipitate is then dissolved in the minimum volume of cold distilled water and dialyzed exhaustively against distilled water in the cold and lyophilized to afford 17 g. of material.

The above material, in 1 g. aliquots, is applied to a 5 × 90 cm. column of Sephadex G-150 (total bed volume of 1,760 cubic centimeters), equilibrated with 50 mM Tris — 100 mM sodium chloride — 0.02% sodium azide, pH 8.0, and the column eluted with the same buffer. The material eluting in the molecular weight range of 40,000-70,000 daltons is collected, desalted by diafiltration through a UM-10 Amicon membrane at 70-80 psi nitrogen pressure, and lyophilized. The total material obtained after all of the 1 g. runs on the Sephadex column is 4 g.

After rechromatography of this material, in 1 g. aliquots as described above, using the same Sephadex column, followed by diafiltration and lyophilization as above, there is obtained 2 g. of material.

The chart below illustrates the weight of material and the activity in the in vitro rosette assay, as described in example 2,

| Material | Dry Weight (Grams) | Activity - Rosette Assay (μgs.) |
|---|---|---|
| Cohn IV-1 | 40 | 12 |
| 40-60% ammonium sulfate precipitate | 17 | 1.6 |

-continued

| Material | Dry Weight (Grams) | Activity - Rosette Assay (μgs.) |
|---|---|---|
| G-150, fraction 3 | 4 | 0.20 |
| G-150, fraction 3, repeat | 2 | 0.02 |

The material from the above procedure may be subjected to preparative polyacrylamide gel electrophoresis and chromatography on a micro column as described in Example 1 to afford the subject material, essentially free of impurities, exhibiting activity in the in vitro rosette assay comparable to that described in Example 2, i.e., from about 0.2 to about 1.0 ng.

EXAMPLE 10

Effect of Human Prealbumin In Vitro on Promoting Maturation of Immunologically Competent Cells Immature thymocytes from normal mice are not normally T cells with significant cytotoxic activity. Acceleration of the maturation of these thymocytes to lymphocytes exhibiting cytotoxic activity is an indication of the enhancement of immunologic competence.

Protocol $1 \times 10^7$ thymocytes from C57B1/6 mice are cultured with $5 \times 10^6$ irradiated Balb/c mouse spleen cells, with and without 5 μg material corresponding to the last step in the chart in Example 9, or 5 μg BSA, for five days. Cytotoxicity is measured on P815 Y(H-$2^d$) cells labeled with $^{51}$Cr.

| | % $^{51}$Cr Release |
|---|---|
| Thymocytes + Balb/c + 5 μg BSA | 15 |
| Thymocytes + Balb/c + 5 μg human prealbumin preparation | 45 |

The data show that lymphoid cells that normally do not exhibit cytotoxic activity show, in the above data, the development of significant cytotoxicity as a result of their exposure in vitro to the human prealbumin preparation.

EXAMPLE 11

As indicated above in Example 5, lymphoid cells from nude mice are generally immunologically unresponsive. A study was conducted of the effect of a human prealbumin preparation on eliciting an immunological response from nude mouse spleen cells incubated in vitro. The mixed lymphocyte reaction (see Example 4, above) was the assay system.

Protocol $5 \times 10^5$ spleen cells of nu/nu mice (Balb/c background) were cultured with $5 \times 10^5$ irradiated F$_1$ (Balb x C57/K6) mouse spleen cells for three days, with tritiated thymidine added for the last four hours. A concentration of 2 μg/tube of human prealbumin preparation (hormone) corresponding to the last step in the chart in Example 9 was utilized. Values are means ± S.E. for three experiments.

| Cell Source | Syngeneic | | Allogeneic | |
|---|---|---|---|---|
| | Hormone | BSA | Hormone | BSA |
| nu/nu spleen | 1241±74 | 1027±95 | 6725±75 | 1567±67 |

The data show that, whereas the nude mouse spleen cells incubated with bovine serum albumin did not respond in the mixed lymphocyte reaction, similar cells incubated with 2 μg of the hormone preparation per $5 \times 10^5$ spleen cells did effectively endow these cells with the capacity to function in the mixed lymphocyte reaction. Thus the hormone converted immunologically non-responsive cells to cells with immunological activity.

EXAMPLE 12

Lymphocyte Autosensitization In Vitro

When lymphoid cells of an animal are allowed to incubate either in vitro or in an enclosed chamber, with nonlymphoid cells of the same animal, a phenomenon occurs that is termed autosensitization. That is, the immunologically active lymphoid cells are capable of recognizing that another type of cell is not identical but, in this sense, is foreign. The fact that this occurs can be assessed by evaluating the degreee of cytotoxicity of these sensitized lymphocytes. This is done by measuring the extent of lysis or "killing" of cells (target cells) to which the lymphocytes have been sensitized by mixing the sensitized cells with the target cells labeled with an isotope, generally a radioactively labeled chromium salt. Following incubation, and as a result of lysis of the target cell, the radioactivity of labeled cells is released into the medium where its quantity can be measured. The percent of total radioactivity released is taken as a measure of the degree of cytotoxicity of the sensitized lymphoid cells (Takagusi, M. and Klein, E., Transplantation, 9:219, 1970).

Protocol

Preparation of peripheral blood lymphocytes: Lymphocytes were separated from whole blood by the method of Ficoll-Isopaque gradient. Boyoum, A., Scand. J. Clin. Lab. Inv., Vol 21 (supp. 97), p. 77 (1968).

Culture media

Fibroblast monolayers and target cells were cultured in Earle's medium plus 10% fetal calf serum (Gibco). Lymphocyte sensitization and the cytotoxicity assay was carried out in RPMI 1640 medium (Gibco) supplemented with 10% human AB positive serum, 2 mM glutamine and 4 mM Hepes buffer (Gibco,.

In vitro sensitization of lymphocytes

Normal skin fibroblasts, used between their 3rd and 10th in vitro passage, were seeded in plastic tissue culture flasks (25 cm$^2$, Falcon, Oxnard, USA). Shortly before they reached confluency, the monolayers were irradiated (4000 R) with and X-ray machine (Siemens, stabilipan 15 mA, 22 KV, Filter Al 1 mm, dose rate 362 R/min, distance: 40 cm). Aliquots of the lymphoid cells (from $10^7$ to $1.5 \times 10^7$) were poured into the flasks with and also without the monolayers. Culture medium was replaced on day 3. On day 6 the lymphocytes were recovered by pipetting and washing with fresh medium. Only a small percentage of the lymphoid cells remained firmly attached to the sensitizing monolayer. The collected lymphocytes were washed twice and counted in the presence of trypan blue to assess viability.

Cell-mediated cytotoxicity assay

Lymphocytes were tested by the method of Takasugi, M. and Klein, E., Transplantation, Vol. 9, p. 219 (1970).

Four hundred target cells (skin fibroblasts) were seeded in a volume of 20 μl per well. After overnight incubation, 50% of the cells were attached. The lymphocytes were added in a volume of 20 μl and the reaction was stopped after 48 hours. The number of remaining target cells was recorded after washing with phosphate buffered saline, pH 7.4, fixing with methanol and staining the plates with Giemsa (Gibco). The cell number in wells exposed to lymphocytes cultured previously without the sensitizing monolayers, was taken as the base line for evaluation of cytotoxicity. The number of cells in wells seeded with sensitized lymphocytes and in medium control wells was therefore compared to this value.

The effect of "hormone" (corresponding to the preparation in step 4 in the chart in Example 2) on the above described autosensitization was tested as follows:

10 μg. of hormone in 0.1 ml. of RPMI 1640 medium was added to sensitization flasks containing 4 ml. culture medium.

In the first two studies (subject C.C.) the hormone was present during the six days of sensitization. In the remaining experiment (subject G.K.) the hormone was present only during the first three days, at which time the medium was replaced. The lymphocytes were removed and tested for their cytotoxic activity as described above.

The results are shown in the following table.

fibrosarcoma tumor cells from mice of same strain) mixed with host spleen cells, in a cell impermeable millipore chamber and then inserting the chamber into the peritoneal cavity of C57B1/6 normal mice or mice of this strain that had been thymectomized at one month of age. The hormone preparation was administered in vivo; 20 μg were injected one hour before and six hours after chamber implantation and then every day until day four of sensitization. Animals were sacrificed on the fifth day; the cells, mostly lymphocytes, were recovered from each chamber and assayed for cytotoxicity, using $^{51}$Cr-labeled fibroblasts (from mice of the same strain) as target cells.

The data obtained are the following:

| Chamber host | Cell no/well Mean ± S.E. | % Reduction[a] |
|---|---|---|
| Tx + hormone* | 429 ± 13 | −2[+] |
| Tx | 294 ± 7 | 30[+++] |
| Intact (Litter mates) | 393 ± 9 | 6[+] |
| b | 420 ± 20 | |

[a] +++, P + <0.001; ++, P <0.01; +, P ≧0.05
b Freshly prepared spleen cells used as controls.
*Corresponding to Step 4 from Chart, Example 2.

The above data indicate that injection of the hormone preparation in vivo in thymectomized mice effectively blocked the development of autosensitization of the

| Lymphocyte Origin | Sensitizing fibroblasts | Addition of hormone* | L/T*** : 200/1 Mean ± S.E. % reduction | Cell number/well L/T : 100/1 Mean ± S.E. % reduction | L/T : 50/1 Mean ± S.E. % reduction |
|---|---|---|---|---|---|
| C.C.** | C.C. | − | 587 ± 17  23[xxx] | 427 ± 27  21[xx] | 505 ± 21  7 |
| C.C. | C.C. | + | 730 ± 41  4 | 544 ± 25  0 | 531 ± 21  2 |
| C.C. | − | | 760 ± 13 | 542 ± 17 | 544 ± 18 |
| − | − | | 736 ± 33  3 | 543 ± 44  0 | 554 ± 8  −2 |
| C.C. | C.C. | − | 360 ± 31  32[xxx] | 333 ± 29  32[xxx] | 446 ± 24  19[xx] |
| C.C. | C.C. | + | 504 ± 39  5 | 503 ± 36  −2 | 544 ± 11  0 |
| C.C. | − | | 529 ± 36 | 491 ± 18 | 552 ± 23 |
| G.K. | G.K. | − | 330 ± 18  32 [xxx] | 228 ± 16  17[x] | 393 ± 14  17[xx] |
| G.K. | G.K. | + | 432 ± 17  10 | 249 ± 13  10 | 459 ± 17  3 |
| G.K. | − | | 482 ± 30 | 276 ± 13 | 474 ± 23 |

Statistical significance:
xxx P <0.001
xx P <0.01
x P <0.05
≦0.05

*10 μg of hormone to sensitization flask. Present throughout 6 days of sensitization in experiments 1 and 2; present only during first 3 days in experiment 3.
**Initials of subject donating cells.
***L/T Lymphocyte-target cell ratio.

It is apparent from the data that additions to the sensitization flasks of 10 μg of the hormone preparation either for the entire 6 days of sensitization or only during the first 3 days of the 6-day sensitization period prevented in both cases the appearance of cytotoxic cells. That is, the hormone preparation blocked the auto-sensitization phenomenon. The data indicate the potential utility of the preparation in preventing or ameliorating an ongoing autosensitization process that may be an etiologic factor in autoimmune diseases.

EXAMPLE 13

Lymphocyte Autosensitization in Vivo

Protocol

The technique utilized in Example 12 was used to examine the effect of the hormone preparation on autosensitization in vivo. In addition, the cardinal role of the thymus gland, and its hormones, influencing this autosensitization was examined. The procedure differs from the above in vitro autosensitization in that autosensitization was achieved by placing the target cells (MC57M chamber containing lymphocytes by the mouse fibrosarcoma cells. These data, together with the above example of blocking by the hormone of autosensitization in vitro, further indicate the potential utility of the hormone preparation in human diseases in which an etiologic component is autoimmunization, i.e., the inability to recognize "self".

EXAMPLE 14

The following illustrates representative pharmaceutical compositions (per dose) of the present invention, illustrated for a preparation corresponding to the last step in the chart in Example 9.

| A. | Human prealbumin preparation | 1.0 | mg. |
|---|---|---|---|
| | Sodium chloride | 9.0 | mg. |
| | Water for injection q.s. | 1.0 | ml. |
| B. | Human prealbumin preparation | 1.0 | mg. |
| | Monobasic sodium phosphate monohydrate | 5.4 | mg. |
| | Dibasic sodium phosphate | 8.66 | mg. |
| | Sodium chloride | 2.52 | mg. |

|   |   |   |   |
|---|---|---|---|
|   | Water for injection q.s. | 1.0 | ml. |
| C. | Human prealbumin preparation | 1.0 | mg. |
|   | Mannitol | 100 | mg. |
|   | Water for injection q.s. | 1.0 | ml. |
| D. | Human prealbumin preparation | 1.0 | mg. |
|   | Monobasic sodium phosphate monohydrate | 5.4 | mg. |
|   | Dibasic sodium phosphate | 8.66 | mg. |
|   | Mannitol | 25 | mg. |
|   | Water for injection q.s. | 1.0 | ml. |

All of the solid ingredients are dissolved in water and lyophilized in a sterile vial. Prior to administering, water is added to dissolve the solids. For vials to be used for multiple dosing, it is preferred that water containing a preservative, e.g., 1.2 mg. methyl paraben/ml. and 0.12 mg. propyl paraben/ml., be used. Reconstituted compositions may be stored at 4° C. for up to two weeks.

We claim as our invention:

1. A pharmaceutical composition useful for increasing immunologic competence comprising a therapeutically effective amount of human serum prealbumin in admixture with a pharmaceutically acceptable non-toxic carrier.

2. A method of increasing immunologic competence in a subject in need of such treatment which method comprises administering to said subject a therapeutically effective amount of human serum prealbumin or a pharmaceutical composition containing same.

3. The method of claim 2 wherein human serum prealbumin is administered in an amount between about 10 pg. and 20 µg/kg/day.

* * * * *